United States Patent
Meybeck et al.

[11] Patent Number: 5,876,758
[45] Date of Patent: Mar. 2, 1999

[54] SOLID COMPLEX PARTICLES COMPRISING A BIOLOGICALLY ACTIVE SOLID SUBSTANCE, MODE OF PREPARATION AND COMPOSITIONS FOR TOPICAL USE CONTAINING THEM AND INTENDED TO TREAT BIOLOGICAL SURFACES

[75] Inventors: Alain Meybeck; Frédéric Bonte, both of Courbevoie, France

[73] Assignee: LVMH Recherche, Nanterre, France

[21] Appl. No.: 266,434

[22] Filed: Jun. 27, 1994

Related U.S. Application Data

[63] Continuation-in-part of Ser. No. 6,204, Jan. 19, 1993, Pat. No. 5,374,452, which is a continuation of Ser. No. 743,285, Jan. 17, 1992, abandoned, said Ser. No. 266,434, Jun. 27, 1994 which is a continuation-in-part of PCT/FR92/01238, Dec. 24, 1992.

[30] Foreign Application Priority Data

| Aug. 4, 1989 | [FR] | France | ................................. 89 10565 |
| Aug. 3, 1990 | [WO] | WIPO | .................... PCT/FR90/00588 |
| Dec. 27, 1991 | [FR] | France | ................................. 91 16265 |

[51] Int. Cl.⁶ .................. A61K 9/16; A61K 9/50
[52] U.S. Cl. ............... 427/490; 424/63; 424/64; 424/65; 424/69; 424/401
[58] Field of Search ................... 427/213, 215, 427/218, 222; 428/407; 424/63, 64, 65, 69, 401, 490

[56] References Cited

U.S. PATENT DOCUMENTS

| 4,016,099 | 4/1977 | Wellman et al. ............ 252/366 |
| 4,209,550 | 6/1980 | Hagenbach et al. ............ 427/180 X |
| 4,233,387 | 11/1980 | Mammino et al. ............ 430/137 |
| 4,438,179 | 3/1984 | Solc ............ 428/407 |
| 4,477,492 | 10/1984 | Bergna et al. ............ 427/215 |
| 4,478,914 | 10/1984 | Goese ............ 418/407 |
| 4,593,007 | 6/1986 | Novinski ............ 501/105 |
| 4,908,391 | 3/1990 | Melber et al. ............ 521/57 |
| 5,017,383 | 5/1991 | Ozawa et al. ............ 424/490 |
| 5,041,334 | 8/1991 | Nakajima et al. ............ 428/407 |
| 5,145,675 | 9/1992 | Won ............ 424/78.31 |
| 5,270,056 | 12/1993 | Berglund ............ 424/490 |
| 5,300,290 | 4/1994 | Spencer ............ 424/54 |
| 5,384,130 | 1/1995 | Kamada ............ 424/490 X |

FOREIGN PATENT DOCUMENTS 0324725  7/1989  European Pat. Off. .

*Primary Examiner*—Michael Lusignan
*Attorney, Agent, or Firm*—Ostrolenk, Faber, Gerb & Soffen, L.L.P.

[57] ABSTRACT

The present invention relates to solid complex particles, each comprised of at least two solid substances, at least one of them being biologically active.

The biologically active solid substance is comprised of at least one biologically active product and is evenly distributed at the surface of a grain consisting of the other solid core-forming substance, so-called support substance, said grain having a size comprised between 0.05 and 100 $\mu$m (microns) and the weight ratio between said active substance and said core-forming substance being comprised between $10^{-4}$ and 1.5 approximately.

The invention also relates to a method for the preparation of said particles, a process for the treatment of a biological surface in order to accelerate the biodisponibility of a biologically active substance.

It also relates to compositions for topical application containing the particles of the invention.

32 Claims, 2 Drawing Sheets

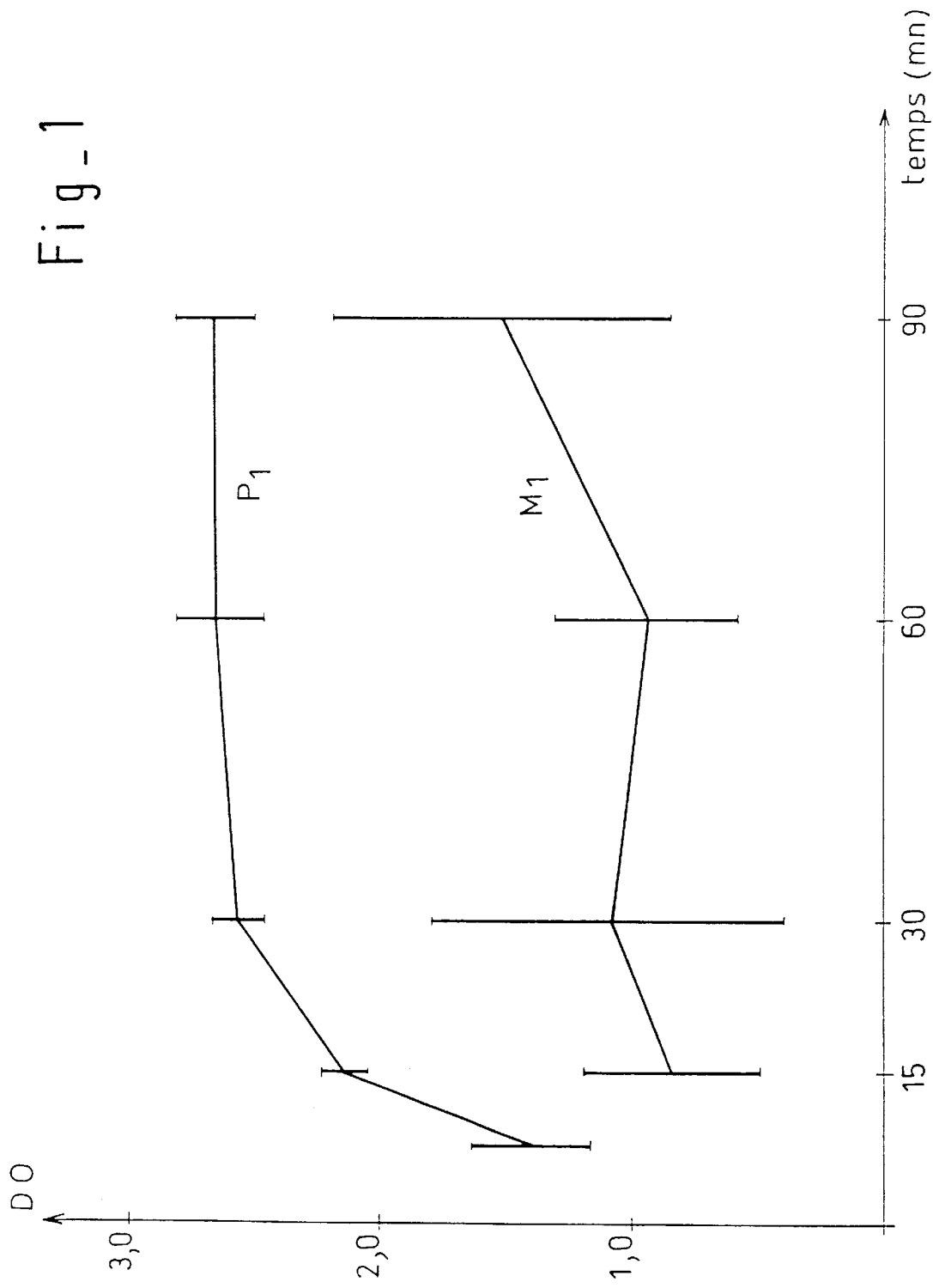

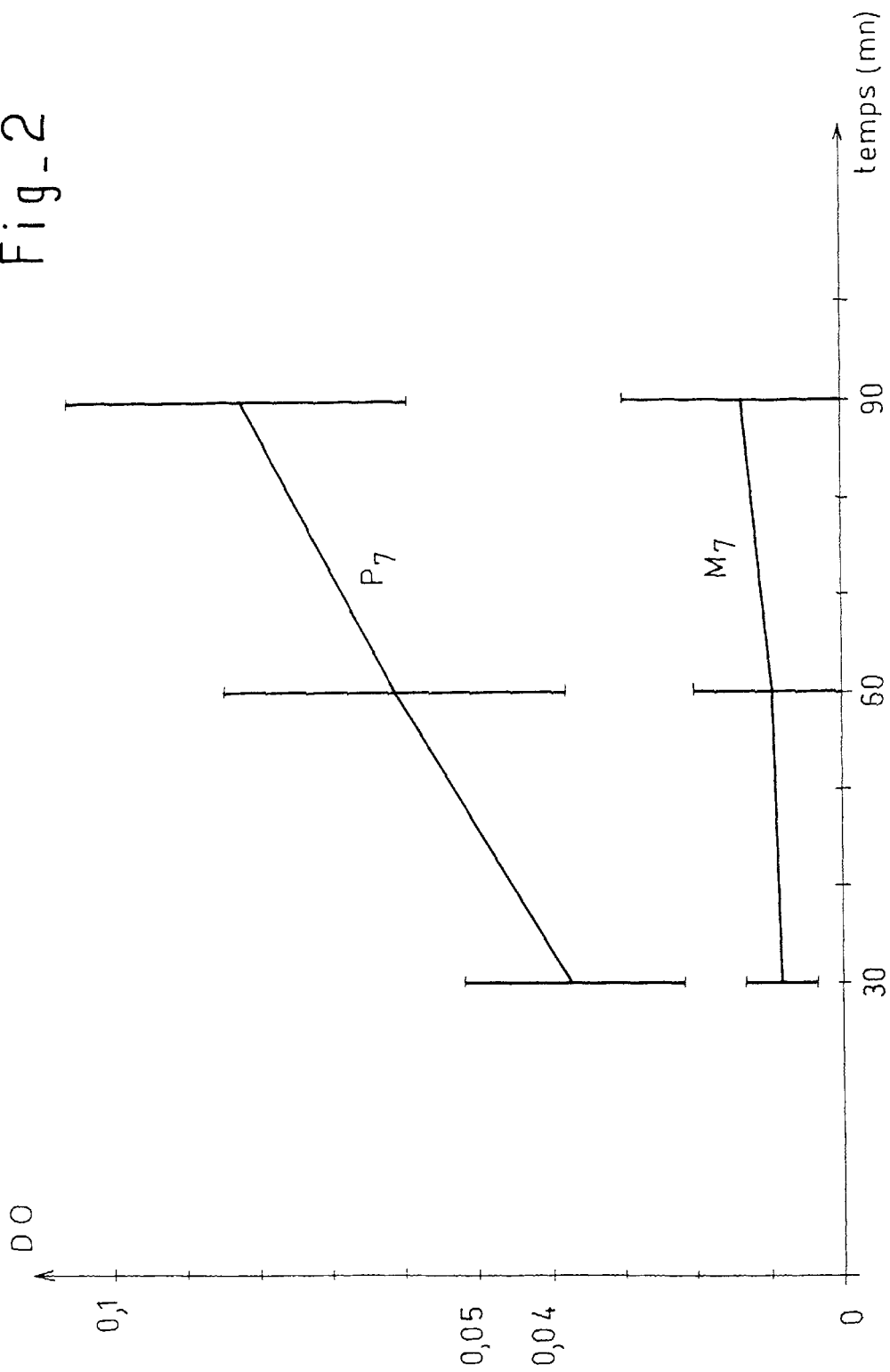

SOLID COMPLEX PARTICLES COMPRISING A BIOLOGICALLY ACTIVE SOLID SUBSTANCE, MODE OF PREPARATION AND COMPOSITIONS FOR TOPICAL USE CONTAINING THEM AND INTENDED TO TREAT BIOLOGICAL SURFACES

The present application is a Continuation-in-Part of U.S. application Ser. No. 08/006,204 filed Jan. 19, 1993, now U.S. Pat. No. 5,374,452, patented Dec. 20, 1994, which is a Continuation application of U.S. Ser. No. 07/743,285, filed Jan. 17, 1992, now abandoned, the full contents of which are incorporated herein by reference.

The present application is further a Continuation-in-Part of PCT application No. PCT/FR92/01238 filed on Dec. 24, 1992, the full content of which is also incorporated herein by reference.

The present invention relates to novel complex particles comprising a biologically active solid substance, to their mode of preparation and to the compositions for topical use containing them and intended for the treatment of biological surfaces.

Biological surfaces will designate living surfaces, in particular the skin, the integuments or the aerial parts of plants.

Biologically active matter is understood to mean any matter capable of having a cosmetic, dermatological or pharmaceutical effect in a composition intended for the treatment of the skin or the integuments, or a plant protective effect in a composition intended for the treatment of the aerial parts of plants.

Certain active products which may be used in the domain of cosmetology or therapeutics or in treatment for protecting plants, are in the solid state. When it is desired to introduce these products in the solid state in formulations intended to be applied over a living surface, and of which a rapid action is expected, a double technological problem is encountered:

1. the most homogeneous possible distribution of the product within the mixture constituting the formula must be ensured, 2. the active product must be able to be released sufficiently rapidly in order to obtain the desired effect of the cosmetic or dermatological products on the skin or the integuments or of the plant-protecting products on the aerial parts of the plants.

When a solid active product is used, it is generally not possible to divide it finely enough for it to be released rapidly and, moreover, it is generally difficult to distribute powder solids uniformly over a surface such as that of the skin.

Various processes for manufacturing solid particles containing a solid active product are known.

In general, it is question of obtaining that the active product be released more slowly than if it were question of the pure product.

For example, French Patent FR-8702695 describes agglomerates of 0.2 to 2 mm comprising in particular particles of active ingredients, designed so that the release of the active ingredients is prolonged upon application thereof on the skin.

Coatings of pharmaceutical products intended to slow down absorption thereof by the organism have also been described, for example in the article by H. TAKEUCHI et al., published in DRUG DEVELOPMENT AND INDUSTRIAL PHARMACY 15 (12) 1999–2016 (1989).

Such particles are not suitable when it is question of obtaining an acceleration of the release of the active ingredients on the skin or on the integuments (hair, lashes and nails in particular). This is the case in particular for a cosmetic product which remains on the skin only for a short time, for example between cleaning thereof in the morning and make-up removal in the evening. This is also the case when the active ingredients are sparingly soluble in the sebum or in the cutaneous humidity.

Applicants have now found novel products making it possible to solve, simultaneously, all these problems not solved by the prior art, by proposing novel products containing a solid active substance of which the release on a living surface such as that of the skin or of the integuments or on the aerial parts of plants is effected at an increased speed.

Moreover, such release is generally reproducible from one application to another, which is advantageous to obtain a satisfactory activity.

The present invention therefore concerns, by way of novel industrial products, complex particles including a solid active matter. It also concerns their process of elaboration and their use particularly in the domain of cosmetology, dermatology and in the treatment of plants, in particular in compositions where the biodisponibility of the active matter with respect to a living surface is increased.

FIG. 1 represents, respectively for the product according to the invention described in example 1 (P1) and for a comparative product (M1) obtained by mixture of the same constituents, the optical density (OD) measured in a Frantz diffusion cell provided with a membrane on which the product is deposited.

FIG. 2 represents, respectively for the product according to the invention described in example 7 (P7) and for a comparative product (M7) obtained by mixture of the same constituents, the optical density (OD) measured in a Frantz diffusion cell provided with a membrane on which the product is deposited.

According to one of the essential characteristics, the object of the present invention is to provide solid complex particles each composed of at least two solid substances of which at least one is biologically active, characterized in that said biologically active solid substance is composed of at least one biologically active product, and is regularly distributed on the surface of a grain constituted by the other solid core-forming substance, called support substance, said grain having a dimension included between 0.05 and 100 $\mu$m (microns), and in that the weight ratio between said active substance and said core-forming substance is included between about $10^{-4}$ and 1.5, which is equivalent to a weight distribution between said substances of about 0.01 for 99.99 to 60 for 40.

According to an advantageous characteristic, the mean dimension of the core of the complex particles according to the invention is included between 0.3 and 30 $\mu$m (microns).

According to another advantageous characteristic, the weight ratio mentioned above is included between $10^{-4}$ and 0.35.

Thus, the particles according to the invention comprise a core constituted by a solid substance serving as support for a biologically active solid substance.

In the following Specification and in the Claims, the expression "support substance" will designate the solid core-forming substance mentioned above.

According to an advantageous characteristic of the invention, the support substance is an insoluble substance.

By way of examples of support substances constituting the core of the particles of the invention, the following will be cited:

synthetic polymers solid at ambient temperature, such as polyamides, polyethylene, polystyrene, polyacrylates, polymethacrylates, minerals such as talc, mica, sericite, vermiculite, pigments such as titanium oxide, iron oxides, sparingly soluble organic substances such as lauryllysine, inorganic or vegetable waxes with a melting point preferably higher than 100° C., natural polymers such as cellulose, natural particles such as walls of yeasts or of euglene.

Such products are available on the market.

By way of products constituting the biologically active solid substance disposed regularly on the grains of the support substance, any biologically active solid matter which may be used in dermatological or cosmetological compositions or in compositions for plant protection, will be cited.

More particularly, among such active products, the following products will be cited:

vitamin phosphates, in particular phosphates of vitamin E or of vitamin C, succinates of tocopherol, polyoxyethylenated or not, glycyrrhizinic acid, its salts and its solid esters, glycyrrhetinic acid, its salts and its solid esters, pulverulent vegetable extracts, particularly extracts of Scutellaria, Phellodendron, Glycyrrhiza, Morus alba, kojic acid and its solid derivatives, ecdysteroids, in particular β-ecdysone and its solid esters, econazol, Minoxidil® solid bactericides for deodorants.

The layer of biologically active substance surrounding the core of each particle according to the invention may also be constituted by a mixture of biologically active products.

The grains of support substance are of any shape, in particular these grains may be of spherical or cubic form or in the form of a disc or a platelet or in any quite irregular shape.

The dimension of these grains is generally included between 0.05 and 100 μm, advantageously between 0.3 and 30 μm.

The active substance mentioned above is distributed regularly on the surface of the grains of the support substance in a relatively fine layer thus forming complex particles. The latter may together form a powder so that, in said powder, the weight ratio of the active substance with respect to the support substance is included between about $10^{-4}$ and 1.5.

This ratio is advantageously included between $10^{-4}$ and 0.35.

According to a variant of the invention, the complex particle according to the invention may comprise, in addition, with the biologically active substance, one or more additives, particularly intended for conservation, coloration or modification of the surface properties of said complex particle.

The invention also concerns a process for obtaining the particles according to the invention.

The process according to the invention makes it possible in particular to distribute the active substance in uniform manner in a very thin layer on the surface of the particles of support substance which themselves are very fine, since they have a mean diameter of 0.05 to 100 μm, and preferably from 0.3 to 30 μm.

The particles according to the invention are advantageously obtained in a process employing a step of atomization of a suspension of the support substance in a solution of the biologically active substance.

In order to obtain the particles according to the invention, the grains of the support substance are dispersed in a liquid containing at least one biologically active substance either in dissolved form or in the form of a very fine dispersion, in order to obtain a suspension of the support substance in said liquid, then atomization of said suspension is effected in order to obtain a powder of particles constituted by grains of support substance regularly coated with the biologically active substance.

A product non-solvent of the support substance will be chosen as liquid for effecting said suspension.

As solvent of the active substance, water or an organic solvent or a mixture of these solvents will for example be chosen.

This solvent will advantageously be chosen so that it is sufficiently volatile to be able to be eliminated during the subsequent step of atomization.

By way of examples of solvents which may be used for placing the active substance in solution, water, dichloromethane, or mixtures thereof with methyl alcohol or ethyl alcohol, will be cited.

The conditions of atomization and possibly the choice of the nature of the substance intended to form the support are generally dictated by the following considerations: atomization is effected at a temperature at least equal to the boiling point of the solvent and substantially less than the temperature of softening of the support.

During the atomization step, the suspension is atomized into very fine droplets in a stream of hot gas, preferably taken to a temperature higher than that of the boiling point of the solvent of said suspension, so that the liquid evaporates rapidly in order that the solid active product be deposited instantaneously and regularly on the surface of the particle.

The desired thickness of the deposit of the active substance on the surface of the support substance may be obtained, with constant droplet size, during atomization, by playing on the following two parameters: concentration of the active substance and concentration of support particles.

The suspension of the support particles in the active substance solution will advantageously comprise a product improving wetting and/or dispersion of said particles in suspension, which promotes a regular and preferential deposit of the active substance on the surface of the particles of support substance.

By way of examples of such products, particular mention will be made of the surface-active agents acceptable for the application envisaged, for example a polyoxyethylenated sorbitan monolaurate, such as MONTANOX 20, or amphiphilic lipids, such as lecithins.

According to another variant of the process according to the invention, the particles according to the present invention may be prepared by a process derived from that described in the French Patent Application filed on Aug. 4, 1989 under No. 89 10565 and published under No. FR 2 650 514.

More precisely, according to this variant, the particles according to the invention may be obtained from a suspension, in a dispersion liquid, containing two populations of solid particles of substantially homogeneous sizes respectively comprising at least one population of support substance and at least one population of biologically active solid substance, the mean size of the particles of active substance preferably being less than or equal to about 0.2 times the mean size of the particles of support substance. In order to obtain the particles according to the present invention, the said suspension is atomized in an enclosure, such as that of an atomization apparatus, under conditions of pressure and temperature which make it possible to obtain the rapid evaporation of the dispersion liquid and the formation of a powder constituted by particles according to the invention.

According to an advantageous variant of the invention, there may be introduced into the product intended to be atomized, different additives such as colorants, agents intended to modify the surface properties of the complex particle or conservation agents.

Furthermore, it has appeared that the complex particles according to the invention made possible a more rapid release of the active substance upon contact with a living surface, such as that of the skin or the integuments, or that of the aerial parts of plants and that, in addition, they allowed a more reliable release of said active substance.

The present invention therefore likewise concerns a process for accelerating the biodisponibility of a biologically active substance contained in a composition intended to be placed in contact with a biological surface, comprising the use, particularly by application on said biological surface, of a composition containing complex particles such as defined hereinbefore.

According to the invention, it is thus possible to obtain a more rapid cosmetic or therapeutic effect at the level of the superficial layers of the biological surface. The same effect of acceleration may in addition be obtained for pharmaceutical compositions for transcutaneous use. The degree of penetration of the biologically active substance may be adjusted by playing on the nature of the constituents used in said composition, which is well known to the man skilled in the art.

Laboratory tests in a FRANTZ diffusion cell provided with a porous membrane of polyvinylidene fluoride, connected to a system of detection by UV/visible spectrometry, have demonstrated the release at increased speed of the active substance with respect to that which would be obtained by simple intimate mixture of the two types of powder.

The invention also concerns compositions for cosmetic or dermatological use or adapted to be used in the domain of plant protection, comprising the complex particles described previously or obtained by the process for preparation described hereinabove.

It is generally question of compositions in solid form. However, it may also be question of compositions in liquid form insofar as the complex particles are not dissolved by the other constituents of the composition.

By way of examples of compositions capable of containing the complex powders of the invention, particular mention will be made of all the cosmetic products for which the conditions of application on the skin allow the presence of particles having the dimensions of the complex particles of the invention and in which the presence of solid biologically active products is desirable.

In particular, it is question of products in pasty or solid form, for example in the form of powder, compacted or not, in the form of paste or in the form of suspension.

By way of examples of such products, the following will be cited: mascaras, eye shadows, cheek blushers, lipsticks, eyelash make-up, foundations, free or pressed powders.

Among the dermatological compositions, antimycotic powders, healing powders, anti-inflammatory talcs, sticks for chapped lips, will be cited.

Among the compositions for use in plant protection, the products for treating the aerial parts of the plants, particularly the leaves and stalks, in pulverulent form, will be cited.

EXAMPLES

EXAMPLE 1

There will be used as support particles spheres of polyamide of Nylon 12 SP 500 (Toray) type, having a mean diameter equal to about 20 $\mu$m, a density of about 1 g/cm$^3$ and a specific surface of 0.68 m$^2$/g, on which is deposited a phosphate of vitamin C in the following manner:

10 g of magnesium salt of ascorbyl phosphate ($C_6H_6O_9P$, 3/2 Mg) (NIKKOL VC PMG®) of density of about 0.5 g/cm$^3$ are dissolved in 200 ml of water heated to 35° C. and stirred;

1 g of monolaurate of polyoxyethylenated sorbitan (MONTANOX 20®) is added;

90 g of Nylon 12 NP 500 are added;

the mixture is completed with water up to a total weight of 500 g;

the mixture is stirred to disperse the powder of polyamide balls and to obtain a homogeneous suspension;

the suspension is atomized by injecting it in a Drytech atomizer, functioning with hot air under a pressure of 7 bars with a temperature adjustment of 150° C. at the entrance of the apparatus and 75° C. at the exit, as well as an injection flowrate of the suspension of about 0.5 1/hr.

In this way, a white powder ($P_1$) is obtained, constituted by particles which prove to be homogeneous in shape and in size by examination with a scanning electron microscope. The phosphate of vitamin C has therefore been deposited regularly on the surface of the Nylon spheres in a proportion by weight of about 10 g of biologically active product for 90 g of support, thus producing complex particles according to the invention. The thickness of active substance distributed on the surface of the Nylon spheres, determined by calculation, is about 0.33 $\mu$m.

EXAMPLE 2

One operates as in Example 1 to manufacture complex particles according to the invention, comprising a proportion by weight of about 10 g of potassium diglycyrrhizinate, of density of about 0.7 g/cm$^3$, for 90 g of spheres of Nylon 12 SP 500.

EXAMPLE 3

One operates as in Example 1 to manufacture complex particles according to the invention comprising a proportion by weight of about 10 g of tocopheryl—sodium phosphate, of density of about 0.6 g/cm$^3$, for 90 g of spheres of Nylon 12 SP 500.

EXAMPLE 4

One uses as support particles of mica, of mica Concorde grade 400 type, in the form of platelets of mean size of 30 $\mu$m and with specific surface of 9.7 m$^2$/g, on which is deposited 18-$\beta$-glycyrrhetinic acid in the presence of soya bean lecithin.

One proceeds as follows:

8 g of soya bean lecithin are dissolved in 200 ml of dichloromethane with stirring, 2 g of 18-$\beta$-glycyrrhetinic acid are added to this solution with stirring, 90 g of platelets of mica are added to this solution, the mixture is completed with dichloromethane up to a total weight of 500 g, the mixture is stirred for 1 hour at 30° C. to facilitate dispersion of the mica and to obtain a homogeneous suspension, this suspension is atomized by injecting it in a Drytech atomizer, functioning with hot air under a pressure of 7 bars, with a temperature adjustment of 80° C. at the entrance of the apparatus and 45° C. at the exit, as well as an injection flowrate of the suspension of about 5 1/hr.

A white powder is thus obtained of which the unitary particles prove to be homogeneous in shape and in size by examination with a scanning electron microscope. The 18-β-glycyrrhetinic acid has therefore deposited with the lecithin in regular manner on the surface of the platelets of mica in a proportion by weight of about 2 and 8 g respectively for 90 g of support.

EXAMPLE 5

One operates as in Example 4 for manufacturing particles according to the invention comprising a proportion by weight of about 2 g of 18-β-glycyrrhetinic acid and 9 g of soja bean lecithin for 90 g of talc of Micro talc IT extra type, with specific surface of about 10 m$^2$/g and whose particles present a roughly paralelepipedic shape and a mean size of 5 μm (microns).

EXAMPLE 6

One operates as in Example 1 to manufacture complex particles according to the invention comprising a proportion by weight of about 10 g of dry extract of Phellodendron for 90 g of particles of polyamide of irregular shape of Orgasol 2002 UD type and of mean size 20 μm. Operation takes place with a gas exit temperature of 70° C.

EXAMPLE 7

One uses as support particles of polyamide (I) of ORGASOL 2002D NAT COS® type, of mean size of about 20 μm. On these particles is deposited a 50:50 by weight mixture (II) of 18-β-glycyrrhetinic acid (III) and of polyoxyethylenated tocopherol succinate (IV).

To that end, one operates as follows:

10 g of IV are solubilized in 800 ml of water at 60° C. with stirring, by means for example of a Rayneri type propeller stirrer.

10 g of III in pulverulent form are added at the same temperature, maintaining stirring, until a substantially homogeneous suspension is obtained. The same conditions always being maintained, 80 g of particles I are dispersed, in small quantities, and stirring is continued until a homogeneous suspension is obtained.

This suspension is then atomized by injecting it in a DRYTECH type atomizer, functioning with hot air under a pressure of 6 bars, with a temperature adjustment of 221° C. at the entrance of the apparatus and 78° C. at the exit, as well as an injection flowrate of the suspension of about 0.5 1/hr.

A fine powder (P$_7$) is thus obtained which is observed under a scanning electron microscope.

This observation shows a very regular distribution of the constituents III and IV on the surface of the particles I, constituent IV being in the form of a thin film, regularly sprinkled with crystals of constituent III.

Furthermore, the dosage of the constituents III and IV in the powder of complex particles according to the invention thus obtained, exactly reflects the initial proportions before atomization.

EXAMPLE 8

Operation is as in Example 1 for manufacturing complex particles according to the invention comprising a proportion by weight of about 25 g of magnesium salt of ascorbyl phosphate and 75 g of polyamide of Nylon 12 type.

EXAMPLE 9

Operation is as in Example 1 for manufacturing complex particles according to the invention comprising a proportion by weight of about 5 g of β-ecdysone and 95 g of cellulose powder of which the grain diameter is included between 50 and 150 μm.

EXAMPLE 10

It is proposed to compare in this Example the speed of release of the magnesium salt of ascorbyl phosphate from the powder (P$_1$) of Example 1, with the speed of release of the same active product contained in an intimate mixture (M$_1$) obtained by crushing with a rapid propeller a mixture of 10 g of magnesium salt of ascorbyl phosphate (C$_6$H$_6$O$_9$P, 3/2 Mg), 1 g of MONTANOX 20® and 90 g of Nylon 12 SP 500, these products thus being in the same proportions as in the powder of complex particles (P$_1$) of Example 1. To that end, a mixer of O.M. DIZER® type (Nara Machinery Co.) is used, comprising on the bottom a rotor with propeller rotating at 1800 rpm and on the side a propeller rotating at 3000 rpm.

Study of the release of the biologically active ingredient is made in a FRANTZ diffusion cell provided with a membrane of hydrophilic/lipophilic polyvinylidene fluoride, of DURAPORE® HVLP 02500 type available from the firm MILLIPORE, of porosity equal to 0.45 μm. The product (or comparative mixture) is deposited on the membrane.

The lower compartment of the cell contains a "sub-phase" constituted by demineralized water at 37° C. stirred by a magnetized bar. This water receives the product which diffuses through the humid membrane. At regular intervals, its optical density is measured by means of an U.V. spectrometer for a wave length of 243 nm. The optical density is a function of the concentration of the active product dissolved in the sub-phase which, in the present case, is the salt of ascorbyl phosphate.

Five tests are made under the same conditions, by applying on the membrane of the FRANTZ cell exactly the same quantity, 20 mg, respectively of the powder P$_1$ and of the comparative mixture M$_1$. The diffusion of the active ingredient through the membrane is observed as a function of the time by measuring the optical density of the sub-phase.

Table I hereinafter gives the mean value of the measurements of optical density as a function of the time from the application on the membrane of the products P$_1$ and M$_1$ respectively.

TABLE I

| | Optical densities (diffusion of NIKKOL VSPMG ®) | | | | |
|---|---|---|---|---|---|
| Time (min.) | 7'30" | 15' | 30' | 60' | 90' |
| P$_1$ | 1.37 ± 0.23 | 2.12 ± 0.08 | 2.56 ± 0.09 | 2.62 ± 0.16 | 2.62 ± 0.16 |
| M$_1$ | | 0.866 ± 0.35 | 1.1 ± 0.71 | 0.91 ± 0.37 | 1.50 ± 0.67 |

The above results are also represented in the form of graphs in FIG. 1 which gives the optical density (OD) as a function of time for products P$_1$ and M$_1$.

From Table I and FIG. 1, it is ascertained that, for $P_1$, the diffusion of the active ingredient through the membrane is much more rapid than for $M_1$. The quantity of active ingredient having diffused is also much greater from the first 30 minutes, and even after 90 mins. Finally, it is observed that the standard deviation of the mean values is much greater for $M_1$ than for $P_1$. This signifies that, whatever the samples of product used, the diffusion of the active ingredient is much more reliable in the case of $P_1$ than in that of $M_1$.

These results obtained with the FRANTZ cell, which makes it possible to reproduce, under similar conditions, the release of an active ingredient applied on the skin or on the mucuses, very clearly show that the complex particles according to the invention allow the release of an active ingredient much more rapidly, more efficiently (in greater quantity) and more reliably.

EXAMPLE 11

Operation is as in Example 10, to compare the process of diffusion of the polyoxyethylenated tocopherol succinate from the powder of complex particles $P_7$ of Example 7, on the one hand, and from the mixture $M_7$ of the same composition, namely 80 g of particles of polyamide (ORGASOL 2002D®), 10 g of 18-β-glycyrrhetinic acid and 10 g of polyoxyethylenated tocopherol succinate.

This mixture $M_7$ is made in the following manner. The tocopherol succinate is melted at 75° C., then homogenized with a little water with the particles of polyamide and the glycyrrhetinic acid. The whole is mixed with a spatula until complete wetting of the powder. This powder is then dried, then crushed with a mortar.

Six tests were made by means of the FRANTZ cell, for powder $P_7$ on the one hand, and for mixture $M_7$ on the other hand.

The diffusion of the polyoxyethylenated tocopherol succinate through the membrane is observed, in a sub-phase constituted by demineralized water, by measuring, as in Example 10, the evolution of the optical density of the sub-phase as a function of time, for a wave length of 280 nm.

Table II hereinafter gathers together the mean values on these tests of the optical densities measured for $P_7$ and $M_7$.

TABLE II

Optical density
(diffusion of polyoxyethylenated tocopherol succinate)

| Time (min.) | 30' | 60' | 90' |
|---|---|---|---|
| $P_7$ | 0.038 ± 0.015 | 0.061 ± 0.024 | 0.082 ± 0.024 |
| $M_7$ | 0.0080 ± 0.005 | 0.0095 ± 0.011 | 0.013 ± 0.017 |

The above results are also shown in the form of graphs in FIG. 2 which gives the optical density (OD) as a function of time for products $P_7$ and $M_7$.

From Table II and FIG. 2, results similar to those obtained in the case of previous Example 10 are noted. In particular, it is observed that, in the case of powder $P_7$, the diffusion of the active ingredient (polyoxyethylenated tocopherol succinate) is much more rapid and in a much greater quantity than in the case of mixture $M_7$.

Furthermore, concerning the other active ingredient, constituted by 18-β-glycyrrhetinic acid, which is in the form of small crystals distributed on the surface of the particles of polyamide, diffusion tests have also be made under conditions similar to those set forth hereinabove, except that the sub-phase is constituted by a 60% volume water-alcohol mixture. The wave length used for measuring the optical density is, here, 252 nm. The results of these tests show in particular that the standard deviations of the mean values of optical density are much smaller for powder $P_7$ than for mixture $M_7$. More precisely, the standard deviations for $M_7$ are from 3 to 4 times greater than for $P_7$, which shows, there again, that the diffusion of the active product is much more reliable for the particles of the invention than for the simple mixture.

EXAMPLE 12

Medicated lipstick

The quantities set forth hereinbelow are indicated in parts by weight.

| * Phase B | |
|---|---|
| Ozokerite | 5.51 |
| Syncrowax BB4 | 7.35 |
| Carnauba wax | 1.05 |
| Candellila wax | 2.10 |
| Q 50158 Wax | 4.68 |
| BHA | 0.02 |
| Nipasol M | 0.05 |
| Crodamol ODL | 6.00 |
| Supermol S | 4.00 |
| Arlamol HD | 14.64 |
| Procas $H_3$ | 10.00 |
| Jojoba oil | 4.00 |
| * Phase A | |
| Castor oil | 30.00 |
| Complex particules according to Example 3 | 10.00 |
| * Phase C | |
| Glycamil | 0.10 |
| Perfume | 0.50 |

Phase A is homogenized by passage in a three-cylinder grinder.

A is added in B melted at 85° C.

C is added in B+A.

Cast in moulds pre-heated to 45° C.

20 minutes spent at −5° C.

Wait of 15 minutes at ambient temperature before demoulding.

EXAMPLE 13

Medicated lipstick

Operation is as in Example 12 to produce the following formula in which the quantities of products are indicated in parts by weight.

| * Phase B | |
|---|---|
| Ozokerite E 622 | 5.78 |
| Synchrowax BB4 | 7.70 |
| Carnauba wax | 1.10 |
| Candellila wax | 2.20 |
| Q 50158 A Wax | 3.85 |
| Phytantriol | 4.95 |
| Supermol S | 4.40 |
| Solulan PB 2 | 1.80 |
| Jojoba oil | 3.15 |
| Schercemol DID | 5.77 |
| Cosbiol | 4.73 |
| Primol 352 | 3.90 |

-continued

| * Phase A | |
|---|---|
| Castor oil | 40.00 |
| Complex particles of Example 2 | 10.00 |
| * Phase C | |
| BHA | 0.02 |
| Nipasol M | 0.05 |
| Perfume | 0.60 |
| | 100.00 |

EXAMPLE 14
Softening lipstick:

Operation is as in Example 12 with a Phase B and a Phase C as in Example 13 and a Phase A of the following composition by weight:

| | |
|---|---|
| Complex particles of Example 7 | 5.00 |
| Coloured pigments and coatings | about 10 depending on the complexion |
| Castor oil | qsp 50.00 |

EXAMPLE 15
Coloured pressed powder for sensitive eyelids:

The following formula is made:

A.

| | |
|---|---|
| Magnesium myristate | 4 |
| Sericite | 22 |
| Silica | 4 |
| Boron nitride | 2 |
| Nipagin M | 0.2 |
| Complex particles of Example 7 | 10 |

B.

| | |
|---|---|
| Mixture of pigments and coloured nacres: | about 15 depending on complexion |

C.

| | |
|---|---|
| Binding agent | 10 |

D.

| | |
|---|---|
| Talc | qsp 100 |

Formula of the binding agent:

| | |
|---|---|
| Glyceryl-stearate | 20 |
| Cetyl alcohol | 10 |
| Marcol 82 | 30 |
| Miglyol 812 | 40 |

A, B and D are mixed in a powder mixer. C is introduced very progressively in the mixture A+B+D.

A+B+D+C are pressed in small cups with the aid of a powder compactor.

EXAMPLE 16
Coloured pressed powder to reduce reactions of intolerance on the eyelids Operation is as in Example 15 to make cups of coloured pressed powder including 10% of complex particles according to Example 3.

EXAMPLE 17
Coloured pressed powder for the face enabling the natural pigmentation to be attenuated Operation is as in Example 15 to make small cups of pressed powder comprising 10% of complex particles obtained according to Example 8.

EXAMPLE 18
Healing dermatological powder

The following formula is made, containing in parts by weight:

| | |
|---|---|
| complex particles obtained in Example 9 | 20.00 |
| pulverulent excipient based on microcrystalline cellulose qsp | 100.00 |

The mixture is made in a powder mixer of conventional type.

EXAMPLE 19
Creme mascara formula:

The above (sic.) percentages are indicated in percentage by weight.

| | |
|---|---|
| Veegum | 2 |
| Carboxymethylcellulose | 0.1 |
| Polynaphthalene sulfonate of sodium | 0.2 |
| Propyleneglycol | 1.4 |
| Beeswax | 6.5 |
| Mineral oil | 3.5 |
| Black pigment | 3.00 |
| Stearic acid | 1.00 |
| Carnauba wax | 5.00 |
| Complex particles of Example 7 | 1.00 |
| Conservation agent | 0.2 |
| Water | qsp 100 |

EXAMPLE 20
Pressed powder to improve the complexion of the face

A) Solid complex particles according to the invention are firstly prepared, in accordance with the process described in Example 1, except that the active substance is constituted not by the magnesium salt of ascorbyl phosphate alone, but by an association with equal weights of this salt with an aqueous extract of mulberry (Morus alba) available on the market, in particular from JAN DEKKER-France.

10 g of this association are, as indicated in Example 1, dispersed in 200 ml of water. The other constituents used are the same as those indicated in this Example, with the same proportions.

B) The solid complex particles thus prepared are then incorporated at a rate of 4% by weight in a conventional formula of pressed face make-up powder. Thanks to the depigmenting properties of the association of active ingredients mentioned above, a medicated cosmetic composition is thus obtained in the form of pressed powder, intended to improve the complexion, whilst contributing to making up the face.

We claim:

1. Solid complex particles each comprising at least two solid substances of which at least one is biologically active, wherein said biologically active solid substance comprises at least one biologically active product and is regularly distributed on the surface of a grain constituted by the other solid substance forming core, called support substance, said core being made of a solid substance insoluble under the conditions of use and having a dimension ranging between 0.3 and 30 $\mu$m (microns) wherein the weight ratio between said active substance and said core-forming substance is between about $10^{-4}$ and 1.5; and wherein the solid complex particles are obtainable by a process comprising the steps of:

(1) preparing a suspension of particles of support substances made of the solid substance insoluble under the conditions of use and having a dimension ranging between 0.3 and 30 μm (microns) in a liquid containing at least one biologically active substance in dissolved form, said liquid not being substantially a solvent of the support substance, and wherein the weight ratio between said active substance and said support substance is between about $10^{-4}$ and 1.5; and (2) atomizing said suspension using an atomizer where atomization is effected at a temperature at least equal to the boiling temperature of said liquid and substantially less than the temperature of softening of said support substance, thereby obtaining said solid complex particles and said biologically active substance is regularly distributed on the surface of a grain constituted by the support substance forming a core, and thereby improving the release rate of the biologically active substance on a biological surface with which said active substance is intended to be placed in contact.

2. Particles according to claim 1, wherein said core is made of an insoluble substance.

3. Particles according to claim 1, wherein the weight ratio between the active substance and the support substance is included between $10^{-4}$ and 0.35.

4. Particles according to claim 1, wherein the said core-forming grains have the form of spheres, discs, cubes, platelets or grains of any irregular forms.

5. Particles according to claim 1, wherein said core forming grains are made of a solid substance selected from the group consisting of synthetic polymers solid at ambient temperature, minerals, pigments, organic substances sparingly soluble in water, inorganic waxes, vegetable waxes, natural polymers and natural particles.

6. Particles according to claim 5, wherein the support substance is a solid selected from the group consisting of polyamides, polyethylene, polystyrene, polyacrylates, polymethacrylates, talc, mica, sericite, vermiculite, titanium oxide, iron oxides, lauryl-lysine, cellulose, walls of yeasts or of euglene.

7. Particles according to claim 1, wherein the biologically active product is selected from the group consisting of vitamin derivatives, succinates of tocopherol, polyoxyethylenated or not, glycyrrhizinic acid, its solid esters and salts, glycyrrhetinic acid, its solid esters and salts, pulverulent vegetable extracts, kojic acid, ecdysteroids, econazol, minoxidil and solid bactericides for deodorants.

8. The solid complex particles according to claim 7, wherein the vitamin derivatives are selected from the group consisting of phosphates of vitamin E or of vitamin C.

9. Particles according to claim 7, wherein the pulverulent vegetable extracts are selected from the group consisting of extracts of Scutellaria, Phellodendron, Glycyrrhiza, Morus alba.

10. Particles according to claim 1, wherein said particles further comprise, with the biologically active substance, one or more additives, intended for conservation, coloration or modification of the surface properties of said complex particles.

11. A method to accelerate the bioavailability of a biologically active substance with respect to a biological surface which consists of treating said biological surface with a composition containing solid complex particles according to claim 1.

12. The method according to claim 11, wherein said biological surface is selected from the group consisting of the skin, the integuments, and the aboveground surface parts of plants.

13. A powder constituted by particles according to claim 1.

14. A composition for topical use intended for the treatment of a biological surface wherein said composition contains particles according to claim 1.

15. Composition according to claim 14, wherein said composition is in the solid state.

16. Composition according to claim 14, wherein said composition is in liquid form and wherein the complex particles are not dissolved by the other constituents of the composition.

17. A process for preparing solid complex particles each comprising at least two solid substances of which at least one is biologically active, wherein:

(1) a suspension of particles of support substances made of a solid substance insoluble under the conditions of use and having a dimension ranging between 0.3 and 30 μm (microns) is prepared in a liquid containing at least one biologically active substance in dissolved form, said liquid not being substantially a solvent of the support substance, and wherein the rate ratio between said active substance and said support substance is ranging between about $10^{-4}$ and 1.5, (2) said suspension is atomized by injecting it in an atomizer where atomization is effected at a temperature at least equal to the boiling temperature of the solvent and substantially less than the temperature of softening of said support substance, thereby obtaining said solid complex particles and said biologically active substance is regularly distributed on the surface of a grain constituted by the support substance forming a core, and thereby improving the release rate of the biologically active substance on a biological surface with which said active substance is intended to be placed in contact.

18. A process according to claim 17, wherein the suspension introduced in the atomizer further contains a product promoting wetting and/or dispersion of the particles in suspension.

19. A process according to claim 17, wherein the product intended to be atomized further contains different additives such as colorants, agents intended to modify the surface properties of the complex particle or conservation agents.

20. A process for preparing solid complex particles each comprising at least two solid substances of which at least one is biologically active, the process comprising the steps of:

(1) preparing a suspension of particles of support substances made of a solid substance insoluble under the conditions of use and having a dimension ranging between 0.3 and 30 μm (microns) in a liquid containing at least one biologically active substance in the form of a dispersion of particles of mean size less than or equal to about 0.2 times the mean size of the particles of the support substance, said liquid not being substantially a solvent of the support substance; and (2) atomizing said suspension using an atomizer where atomization is effected at a temperature at least equal to the temperature of boiling of said liquid and substantially less than the temperature of softening of said support substance, thereby obtaining said solid complex particles comprising at least one biologically active product regularly distributed on the surface of a grain constituted by said support substance forming a core, and thereby improving the release rate of the biologically active substance on a biological surface with which said active substance is intended to be placed in contact.

21. The process according to claim 20, wherein the suspension introduced in the atomizer further contains a product promoting wetting and/or dispersion of the particles in suspension.

22. A process according to claim 20, wherein the product intended to be atomized further contains different additives such as colorants, agents intended to modify the surface properties of the complex particle or conservation agents.

23. Solid complex particles each comprising at least two solid substances of which at least one is biologically active, wherein said biologically active solid substance comprises at least one biologically active product and is regularly distributed on the surface of a grain constituted by the other solid substance forming core, called support substance, said core being made of a solid substance insoluble under the conditions of use and having a dimension ranging between 0.3 and 30 $\mu$m (microns), wherein the weight ratio between said active substance and said core-forming substance is between about $10^{-4}$ and 1.5; and wherein it is obtainable by a process comprising the steps of:

(1) preparing a suspension of particles of support substances made of the solid substance insoluble under the conditions of use in a liquid containing at least one biologically active substance in the form of a dispersion of particles of mean size less than or equal to about 0.2 times the mean size of the particles of the support substance, said liquid not being substantially a solvent of the support substance; and (2) atomizing said suspension by injecting it in an atomizer where atomization is effected at a temperature at least equal to the boiling temperature of the solvent and substantially less than the temperature of softening of said support substance, thereby obtaining said solid complex particles comprising at least one biologically active product regularly distributed on the surface of a grain constituted by said support substance forming a core, and thereby improving the release rate of the biologically active substance on a biological surface with which said active substance is intended to be placed in contact.

24. The solid complex particles according to claim 23, wherein said core is made of an insoluble substance.

25. The solid complex particles according to claim 23, wherein the weight ratio between the active substance and the support substance is between $10^{-4}$ and 0.35.

26. The solid complex particles according to claim 23, wherein the core-forming substance has the form of spheres, discs, cubes, platelets or grains of any irregular shape.

27. The solid complex particles according to claim 23, wherein the core-forming substance is made of a solid substance selected from the group consisting of synthetic polymers solid at ambient temperature, minerals, pigments, organic substances sparingly soluble in water, inorganic waxes, vegetable waxes, natural polymers and natural particles.

28. The solid complex particles according to claim 27, wherein the support substance is a solid selected from the group consisting of polyamides, polyethylene, polystyrene, polyacrylate, polymethacrylates, talc, mica, sericicte, vermiculite, titanium oxide, iron oxides, lauryl-lysine, cellulose, walls of yeasts or of euglene.

29. The solid complex particles according to claim 23, wherein the biologically active product is selected from the group consisting of vitamin derivatives, succinates of tocopherol, polyoxyethylenated or not, glycyrrhizinic acid, its solid esters and salts, glycyrhetinic acid, its solid esters and salts, pulverulent vegetable extracts, kojic acid, ecdysteroids, econazol, minoxidil and solid bactericides for deodorants.

30. The solid complex particles according to claim 29, wherein the vitamin derivatives are selected from the group consisting in phosphates of vitamin E or of vitamin C.

31. The solid complex particles according to claim 29, wherein the pulverulent vegetable extracts are selected from the group consisting of extracts of Scutellaria, Phellodendron, Glycyrrhiza, and Morus alba.

32. The solid complex particles according to claim 23, wherein said solid complex particles further comprise, with the biologically active substance, one or more additives, intended for conservation, coloration or modification of the surface properties of said solid complex particles.

* * * * *